United States Patent [19]

Schneider et al.

[11] 4,154,755
[45] May 15, 1979

[54] MANUFACTURE OF N-(2-CYANOPHENYL)-FORMAMIDINES

[75] Inventors: Dieter Schneider; Horst Scheuermann, both of Ludwigshafen, Fed. Rep. of Germany

[73] Assignee: BASF Aktiengesellschaft, Ludwigshafen, Fed. Rep. of Germany

[21] Appl. No.: 796,551

[22] Filed: May 13, 1977

[30] Foreign Application Priority Data

Jun. 23, 1976 [DE] Fed. Rep. of Germany ....... 2628055

[51] Int. Cl.$^2$ ............................................. C07C 123/00
[52] U.S. Cl. ............................ 260/465 B; 260/465 E; 260/564 RF; 542/423
[58] Field of Search ......... 260/564 RF, 465 E, 465 B; 542/423

[56] References Cited

FOREIGN PATENT DOCUMENTS 2115625  10/1972  Fed. Rep. of Germany.

OTHER PUBLICATIONS

Jacobs, J. Heterocyclic Chem. 7 (1970), pp. 1337–1345.
Staiger et al., J. Org. Chem. 13 (1948), pp. 347–352.

Primary Examiner—Arthur P. Demers
Attorney, Agent, or Firm—Keil, Thompson & Shurtleff

[57] ABSTRACT

N',N'-disubstituted N-(2-cyanophenyl)-formamidines are manufactured by reacting isatoic anhydrides with ammonia and then with a mixture of acid halides and formamides.

The N-(2-cyanophenyl)-formamidines which may be manufactured by the process of the invention are valuable starting materials for the manufacture of dyes, crop protection agents and drugs.

11 Claims, No Drawings

MANUFACTURE OF N-(2-CYANOPHENYL)-FORMAMIDINES

The present invention relates to a new process for the manufacture of N',N'-disubstituted N-(2-cyanophenyl)-formamidines by reacting isatoic anhydrides with ammonia and then with a mixture of acid halides and formamides.

J. prakt. Chem., [2], 30 (1884), 467 et seq., and J. org. Chem., 13 (1948), 347 et seq. and 24 (1959), 1,214 et seq. disclose that isatoic anhydride reacts with aqueous ammonia to give anthranilamide and o-ureidobenzoic acid. The reaction of 5,7-dichloroisatoic anhydride with ammonia gives 6,8-dichlorobenzoyleneurea (J. org. Chem., 3 (1938), 414 et seq., and 12 (1947), 743 et seq.), whilst other chlorine-substituted isatoic anhydrides give only moderate yields of chlorinated anthranilamides (J. Org. Chem., 26 (1961), 613 et seq.).

German Laid-Open Application DOS No. 2,115,625 discloses the reaction of anthranilamides with a N,N-disubstituted formamidine chloride to give N-o-cyanophenyl-N',N'-disubstituted formamidines.

We have found that N-(2-cyanophenyl)-formamidines of the formula

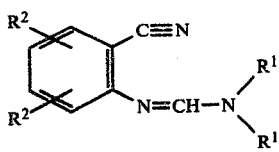

I where the individual radicals $R^1$ may be identical or different and each is hydrogen, an aliphatic radical, an araliphatic radical or an aromatic radical or together with the adjacent nitrogen are members of a heterocyclic ring, and the individual radicals $R^2$ may be identical or different and each is hydrogen, halogen, an aliphatic radical, alkoxy, cyano or nitro, are obtained in an advantageous manner when a corresponding isatoic anhydride of the formula

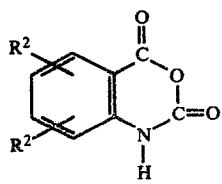

II where $R^2$ has the above meaning, is reacted, in a first step, with ammonia, and this reaction mixture is reacted, in a second step, with mixture of an acid halide of phosphorous acid, phosphoric acid, carbonic acid, oxalic acid, sulfurous acid or sulfuric acid and a formamide of the formula

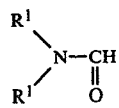

III where $R^1$ has the above meaning.

If isatoic anhydride, dimethylformamide and phosgene are used, the reaction may be represented by the following equation:

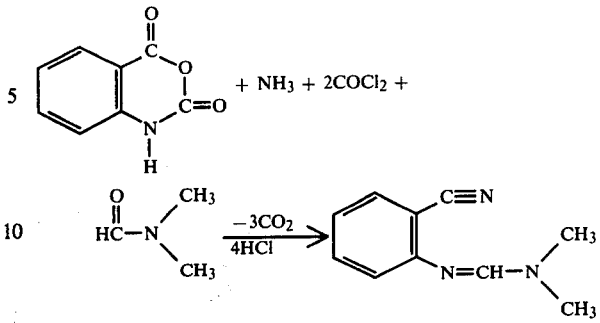

In comparison to the conventional processes, the process of the invention gives N-(2-cyanophenyl)-formamidines more simply and more economically, in good yield and high purity, and with a better space-time yield. The manufacture of the anthranilamides, and the separation and purification operations associated with their isolation, are dispensed with. Since these isolation procedures produce large amounts of inorganic salt, the process according to the invention is also more advantageous from the point of view of the purification of effluent, and the protection of the environment. When synthesizing the anthranilamide, the end product cannot be isolated completely, because of its solubility in the aqueous reaction mixtures or the media used for working up; the total yield, based on the corresponding isatoic anhydride is therefore better in the case of the process of the invention than in the case of a two-stage method. All these advantageous results are surprising in view of the prior art, since secondary reactions, between the formamide and/or acid halide and the reaction products resulting from the reaction of isatoic anhydride with ammonia would have been expected, and hence, at the very least, a substantial deterioration in yield, and the formation of a heterogeneous reaction mixture of numerous components, which were difficult to separate, would have been anticipated.

The starting material II is reacted with ammonia and the mixture of acid halides and starting materials III in stoichiometric amounts or in excess, preferably in a ratio of from 1 to 10, especially from 1 to 3, moles of ammonia per mole of starting material II, in a ratio of from 2 to 10, especially from 2 to 3, equivalents of acid halide per mole of starting material II, and in a ratio of from 1 to 20, especially from 1 to 8, moles of formamide III per mole of starting material II. Preferred starting materials II and III and, accordingly, preferred end products I are those where the individual radicals $R^1$ may be identical or different and each is hydrogen, alkyl of 1 to 8, especially of 1 to 4, carbon atoms, aralkyl of 7 to 12 carbon atoms or phenyl, or together with the adjacent nitrogen form members of a 5-membered or 6-membered, saturated, heterocyclic ring, which may contain a further nitrogen, or an oxygen, and the individual radicals $R^2$ may be identical or different and each is hydrogen, alkyl of 1 to 4 carbon atoms, bromine, chlorine, alkoxy of 1 to 4 carbon atoms, cyano or nitro. The said radicals and rings may be further substituted by groups which are inert under the reaction conditions, e.g. alkyl or alkoxy, each of 1 to 4 carbon atoms.

Examples of suitable starting materials II are (using the numbering

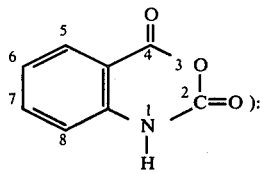

6-chloro-, 7-chloro-, 8-chloro-, 5-chloro-, 6,8-dichloro-, 6-nitro-, 7-nitro-, 5-nitro-, 6,7-dichloro-, 6,8-dinitro-, 6-chloro-8-nitro-and 6-nitro-7-chloro-isatoic anhydride; isatoic anhydrides correspondingly monosubstituted in the 5-position, 6-position, 7-position or 8-position or disubstituted in the 5,6-position, 6,7-position, 7,8-position, 5,7-position, 5,8-position, or 6,8-position by bromine, methyl, ethyl, n-propyl, isopropyl, n-butyl, isobutyl, sec.-butyl, tert.-butyl, methoxy, ethoxy, n-propoxy, isopropoxy, n-butoxy, isobutoxy, sec.-butoxy, tert.-butoxy or cyano; and isatoic anhydrides substituted correspondingly with 2 of the above substituents which are, however, different from one another; isatoic anhydride, 6-chloroisatoic anhydride, 6-nitroisatoic anhydride, 6,8-dinitroisatoic anhydride and 6,8-dichloroisatoic anhydride are preferred.

The following formamides are examples of suitable starting materials III: formamide, formanilide, N-formylpiperidine, N-formylpyrrolidine, N-formylmorpholine, N,N-diethylformamide, N-isobutylformamide, N-methylformamide, form-(p-chloro)-anilide, N,N-dibenzylformamide and especially N-methylformanilide or N,N-dimethylformamide.

The ammonia may be introduced in the solid, liquid or, advantageously, gaseous form; compounds which form ammonia under the reaction conditions, e.g. ammonium carbonate, ammonium carbamate or ammonium acetate, may also be used. Preferred acid halides are acid bromides and especially acid chlorides, advantageously oxalyl chloride, oxalyl bromide, thionyl chloride, phosphorus trichloride, phosphorus tribromide, sulfuryl chloride and especially phosphorus oxychloride or phosgene. The acid halide is generally used in the stoichiometric amount of in excess relative to the starting material III, advantageously in an amount of from 2 to 3 moles of acid halide per mole of starting material III. In the process according to the invention, the acid halide and starting material III are first reacted with one another, and in this way the adducts known for the Vilsmeier process may be manufactured. These adducts may, for example, be represented by the following formula when using phosphorus oxychloride:

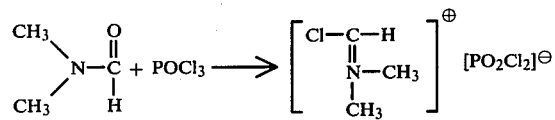

However, the adduct need not have the above structure in every case, nor is the formation of an adduct a precondition of the feasibility of the process of the invention.

The reaction is as a rule carried out at from −15° to +100° C. in both steps, preferably at from 60° to 90° C. in the first step and at from 0° to 40° C. in the second step, under atmospheric or super-atmospheric pressure, continuously or batchwise. Organic solvents which are inert under the reaction conditions can be used, especially in the case of gaseous acid halides. Examples of suitable solvents are aromatic hydrocarbons, e.g. toluene, ethylbenzene, o-, m- and p-xylene, isopropylbenzene and methylnaphthalene, halohydrocarbons, especially chlorohydrocarbons, e.g. tetrachloroethylene, methylene chloride, chloronaphthalene, dichloronaphthalene, carbon tetrachloride, 1,1,1- or 1,1,2-trichloroethane, trichloroethylene, cis-dichloroethylene, o-, m- and p-difluorobenzene, 1,2-dichloroethane, 1,2-cis-dichloroethylene, n-butyl chloride, 2-, 3- and isobutyl chloride, chlorobenzene, fluorobenzene, bromobenzene, iodobenzene, o-, p- and m-dichlorobenzene, o-, p- and m-dibromobenzene, o-, m- and p-chlorotoluene and 1,2,4-trichlorobenzene; ethers, e.g. ethyl propyl ether, methyl tert.-butyl ether, n-butyl ethyl ether, di-n-butyl ether, diisobutyl ether, diisoamyl ether, diisopropyl ether, anisole, phenetole, cyclohexyl methyl ether, diethyl ether, ethylene glycol dimethyl ether, tetrahydrofuran, dioxane and thioanisole; aliphatic or cycloaliphatic hydrocarbons, e.g. heptane, pinane, nonane, gasoline fractions with boiling ranges of from 70° to 190° C., cyclohexane, methylcyclohexane, petroleum ether, decalin, pentane, hexane, naphtha, 2,2,4-trimethylpentane, 2,2,3-trimethylpentane, 2,3,3-trimethylpentane and octane; N-methylpyrrolidone; and mixtures of the above. The solvent is advantageously used in an amount of from 200 to 10,000 percent by weight, preferably of from 300 to 500 percent by weight, based on starting material II. All or part of the solvent may be added to the starting mixture, or all the solvent may be added to the mixture of acid halide and formamide before starting the second step. In a preferred embodiment, the formamide reactant III, e.g. dimethylformamide or formamide, is used as the solution medium. In such cases the formamide III is advantageously used in a total amount of from 300 to 500 percent by weight, based on starting material II; the acid halide may be mixed with the total amount of formamide, or, advantageously, a part, e.g. from half to one-quarter, of the total amount of the formamide may be added to the starting material II before starting the first step.

The reaction can be carried out by taking the starting material II with or without solvent and/or starting material III, then adding ammonia, and finally adding the mixture of acid halide and formamide III. In a preferred embodiment, the mixture of starting material II and ammonia, with or without solvent and/or a part of the starting material III, is kept at the reaction temperature for from 60 to 200 minutes, and any residual free ammonia is flushed out by means of an inert gas, e.g. nitrogen, or by means of air. The mixture of the starting material II is now advantageously added to a mixture of acid halide and starting material III, with or without solvent; under certain circumstances, it is, however, also possible to add the above mixture of the starting material III slowly, in portions, to the mixture containing the starting material II. The total reaction mixture is finally kept at the reaction temperature for from 40 to 200 minutes. The end product is then isolated from this mixture by conventional methods, for example by neutralising with aqueous alkali, e.g. sodium hydroxide solution, and filtering.

The N-(2-cyanophenyl)-formamidines which may be manufactured by the process of the invention are valuable starting materials for the manufacture of dyes, crop protection agents and drugs. Regarding their use, reference may be made to the publications mentioned above. For example, the compounds may be hydrolysed in an acid medium to give the o-aminobenzonitriles, described in German Laid-Open Application DOS No. 2,115,624, which are used for the manufacture of dyes and drugs.

In the Examples which follow, parts are by weight and bear the same relation to parts by volume as that of the kilogram to the liter.

EXAMPLE 1

815 parts of isatoic anhydride are suspended in 615 parts of dimethylformamide at 25° C. The mixture is heated at 60° C. for 20 minutes and 85 parts of ammonia are then passed in over 2.5 hours, during which the temperature rises to 87° C. The suspension is converted to a deep brown solution. After completion of the reaction, 40,000 parts by volume of nitrogen are blown through the solution at 80° C. to remove free ammonia. About 1,400 parts of solution (solution A) are obtained.

1,400 parts of phosgene are passed into 1,925 parts of dimethylformamide at an internal temperature of 20° C., whilst cooling with ice. The mixture is then stirred for 10 minutes, dry nitrogen is passed through the suspension for 5 minutes, and solution A is added over 90 minutes. The temperature is kept at 30° C. by cooling with ice. The mixture is then stirred for a further 10 minutes and introduced into 6,200 parts of water, the batch is brought to pH 7, at 30° C., by adding 2,020 parts of 50 percent strength sodium hydroxide solution, and the end product I is filtered off and washed with 300 parts of water. The yield is 736 parts of N-(2-cyanophenyl)-N',N'-dimethylformamidine of melting point 61°–63° C. (85% of theory, based on isatoic anhydride).

EXAMPLE 2

163 parts of isatoic anhydride are suspended in 138 parts of dimethylformamide and 192 parts of ammonium carbonate are added, starting at 60° C. $CO_2$ is evolved; the temperature rises to 80° C. After 6 hours at 80° C., the solution obtained is reacted as described in Example 1. 144 parts of N-(2-cyanophenyl)-N',N'-dimethylformamidine (83% of theory) of melting point 62° C. are obtained.

EXAMPLE 3

815 parts of isatoic anhydride are suspended in 600 parts of N-methylpyrrolidone at 25° C. Thereafter, the reaction is carried out as described in Example 1. 720 parts of N-(2-cyanophenyl)-N,N'-dimethylformamidine (83% of theory) of melting point 60°–63° C. are obtained.

EXAMPLE 4

163 parts of isatoic anhydride are suspended in 131 parts of dimethylformamide and 156 parts of ammonium carbamate are added, starting at 60° C. Thereafter the reaction is carried out as described in Example 2. 147 parts of N-(2-cyanophenyl)-N',N'-dimethylformamidine (85% of theory) of melting point 61°–63° C. are obtained.

EXAMPLE 5

The reaction is carried out as described in Example 1, but with 988 parts of 6-chloroisatoic anhydride. 832 parts of N-(2-cyano-4-chlorophenyl)-N',N'-dimethylformamidine (80% of theory) of melting point 73°–75° C. are obtained.

EXAMPLE 6

The reaction is carried out as described in Example 1, but with 1,040 parts of 6-nitroisatoic anhydride. 895 parts of N-(2-cyano-4-nitrophenyl)-N',N'-dimethylformamidine (82% of theory) of melting point 140°–142° C. are obtained.

EXAMPLE 7

The reaction is carried out as described in Example 1, with 2,140 parts of phosphorus oxychloride. 692 parts (80% of theory) of N-(2-cyanophenyl)-N',N'-dimethylformamidine of melting point 60°–63° C. are obtained.

EXAMPLE 8

The reaction is carried out as described in Example 6, with 1,840 parts of phosphorus oxychloride. 872 parts (80% of theory) of N-(2-cyano-4-nitrophenyl)-N',N'-dimethylformamidine of melting point 140°–141° C. are obtained.

EXAMPLE 9

The reaction is carried out as described in Example 4, with 233 parts of 6,8-dichloroisatoic anhydride and 114 parts of ammonium carbonate. 200 parts of N-(2-cyano-4,6-dichlorophenyl)-N',N'-dimethylformamidine (82% of theory) of melting point 119° C. are obtained.

We claim:

1. A process for the manufacture of N-(2-cyanophenyl)-formamidines of the formula

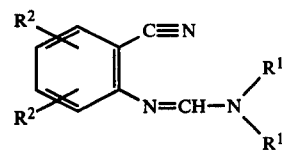

I where the individual radicals $R^1$ may be identical or different and each is hydrogen, alkyl of 1 to 8 carbon atoms, aralkyl of 7 to 12 carbon atoms or phenyl, and the individual radicals $R^2$ may be identical or different and each is hydrogen, alkyl of 1 to 4 carbon atoms, bromine, chlorine, alkoxy of 1 to 4 carbon atoms, cyano or nitro, wherein the said radicals $R^1$ and $R^2$ may be further substituted on the carbon atoms by alkyl or alkoxy, each of 1 to 4 carbon atoms, which comprises:

(a) reacting, in a first step, an isatoic anhydride of the formula

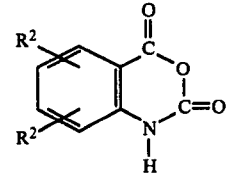

II where $R^2$ has the above meanings with ammonia in non-aqueous phase at 60°–90° C., and subsequently (b) reacting, in a second step, the reaction mixture obtained from step (a) with a mixture of an acid halide of phosphorous acid, phosphoric acid, carbonic acid, oxalic acid, sulfurous acid or sulfuric acid and a formamide of the formula

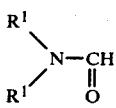

where R¹ has the above meaning.

2. A process as set forth in claim 1, wherein the reaction is carried out with a ratio of from 1 to 10 moles of ammonia per mole of starting material II.

3. A process as set forth in claim 1, wherein the reaction is carried out with a ratio of from 2 to 10 equivalents of acid halide per mole of starting material II.

4. A process as set forth in claim 1, wherein the reaction is carried out with a ratio of from 1 to 20 moles of formamide III per mole of starting material II.

5. A process as set forth in claim 1, wherein the reaction is carried out with oxalyl chloride, oxalyl bromide, thionyl chloride, phosphorus trichloride, phosphorus tribromide, sulfuryl chloride, phosphorus oxychloride or phosgene.

6. A process as set forth in claim 1, wherein the reaction is carried out with from 2 to 3 moles of acid halide per mole of starting material III.

7. A process as set forth in claim 1, wherein the reaction is carried out at from −15° to 100° C. in the second step.

8. A process as set forth in claim 1, wherein the reaction is carried out at from 0° to 40° C. in the second step.

9. A process as set forth in claim 1, wherein the reaction is carried out with organic solvents which are inert under the reaction conditions.

10. A process as set forth in claim 1, wherein the reaction is carried out with the formamide reactant III as the solution medium, using a total amount of from 300 to 500 percent by weight, based on starting material II.